United States Patent [19]

Maxwell et al.

[11] 3,968,243

[45] July 6, 1976

[54] SUBSTITUTED GUANIDINE COMPOUNDS IN THE TREATING OF ARRYTHMIAS

[75] Inventors: Robert Arthur Maxwell, Raleigh, N.C.; Eric Walton, Wrotham, England

[73] Assignee: Burroughs Wellcome Co., Research Triangle Park, N.C.

[22] Filed: Jan. 21, 1974

[21] Appl. No.: 434,947

Related U.S. Application Data

[62] Division of Ser. No. 150,185, June 4, 1971, abandoned.

[30] Foreign Application Priority Data

June 5, 1970 United Kingdom............... 27220/70
June 5, 1970 United Kingdom............... 27221/70
June 5, 1970 United Kingdom............... 27222/70

[52] U.S. Cl. ................................................ 424/326
[51] Int. Cl.² .................................... A61K 31/155
[58] Field of Search .................................... 424/326

[56] References Cited

UNITED STATES PATENTS 3,168,562   2/1965   Walton .............................. 424/326

OTHER PUBLICATIONS

Chem. Abst., vol. 64, 15776b, 1966.

Primary Examiner—Stanley J. Friedman
Attorney, Agent, or Firm—Donald Brown

[57] ABSTRACT

N- substituted - guanidines having antifibrillatory activity; non-toxic salts thereof; pharmaceutical compositions thereof; and their use in treating cardiac fibrillations.

26 Claims, No Drawings

SUBSTITUTED GUANIDINE COMPOUNDS IN THE TREATING OF ARRYTHMIAS

This is a division of application Ser. No. 150,185, filed on June 4, 1971, now abandoned.

This invention relates to guanidine compounds useful in the treatment of cardiac arrhythmias.

It has previously been proposed to employ the powerful hypotensive drug bethanidine (N-benzyl-N', N''-dimethylguanidine) sulphate in the treatment of cardiac arrhythmia. [see "Bethanidine: a New Anti-fibrillatory Agent", Arch. Int. Pharmacodyn., 1966, Vol. 163, pp. 422-426.] The drug has potent antiarrhythmic properties but the hypotensive action attributable to sympathetic blockade causes an undesirable and substantial lowering of blood pressure. Thus, it is essential, when the drug is used, for the patients to be in intensive-care units of hospitals.

It has now been found that the compounds of formula (I), as defined below, possess unexpected advantages over bethanidine in the treatment of arrhythmia. The compounds of formula (I) not only have antiarrhythmic properties comparable to bethanidine, but also have significantly less sympathetic blocking action, thus making possible the treatment of heart disorders with little or no adverse effect on blood pressure.

Among the types of arrhythmias which the compounds of this invention are effective in suppressing are ventricular fibrillations and atrial fibrillations. It has been found that an effective amount of the compounds, which are most desirably pharmacologically and pharmaceutically acceptable salts according to this invention, may be used to treat and suppress ventricular and atrial fibrillations in mammals, such as humans, dogs, cats and the like.

The compounds of formula (I) comprise the bases and acid addition salts of the formula

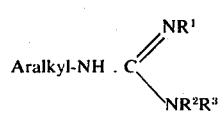

wherein 'Aralkyl' is unsubstituted benzyl, 4-hydroxybenzyl, 4-iodobenzyl or β-phenylethyl, two of the groups $R^1$, $R^2$ and $R^3$ are methyl and the remaining group is hydrogen, provided always that $R^2$ and $R^3$ are both methyl when 'Aralkyl' is unsubstituted benzyl.

The activity of the compounds of formula (I) resides in the base, the nature of the salt only being important for administration requirements. Administration of the compounds will often be over a prolonged period and in such cases the salt must be pharmacologically acceptable, that is, non-toxic, "non-toxic" meaning having no harmful effect on the patient after prolonged treatment, and as used herein the term "non-toxic" has this meaning. Bromides and iodides have physiological activity inherent in their anions which may be undesirable especially upon prolonged administration.

Salts of the bases of the above formula, which are especially preferred for therapeutic use, are the chlorides, sulphates and sulphonates such as the p-toluenesulphonate.

The compounds of formula (I) may be prepared by any method known for the preparation of compounds of analogous chemical structure.

Thus the compounds of formula (I) may be prepared by the reaction of an appropriate lesser-substituted guanidine with a compound Aralkyl X or methyl X, as appropriate, wherein X is a proton-accepting group or atom such as a sulphonate or halogen atom. Such a reaction is preferably carried out in a basic medium. This reaction is exemplified by the reaction diagram:

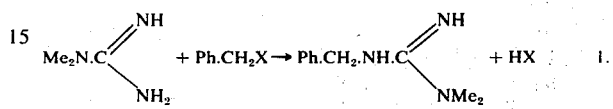

wherein X has the above meaning; and by the reaction diagram:

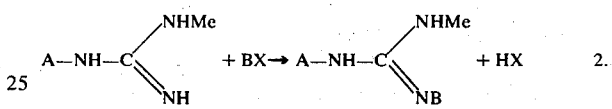

wherein one of A and B is the Aralkyl group other than unsubstituted benzyl and the other is the methyl group, and X has the above meaning.

As another example, the compounds of formula (I) may be produced by the reaction of an appropriate amine or a salt thereof with an S-substituted isothiourea or salt thereof, an O-substituted isourea or salt thereof, or a formamidine substituted by an unsaturated heterocyclic group containing at least two nitrogen atoms in the ring, one of which is attached to the carbon atom of the formamidine structure. These reactions may be illustrated by the following reaction diagram:

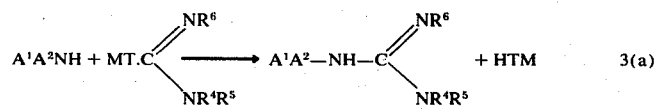

wherein one of $A^1$ and $A^2$ or of $R^4$ and $R^5$ is unsubstituted benzyl and the other and $R^6$ is hydrogen and the two remaining groups are methyl; or $A^1$ and $A^2$ are hydrogen, $R^6$ is unsubstituted benzyl and $R^4$ and $R^5$ are methyl; M is a hydrocarbon (substituent) group and T is an oxygen or a sulphur atom. M is preferably an alkyl group of one to four carbon atoms, especially methyl or ethyl; either the amine or the urea derivative is advantageously present as an acid addition salt such that during the reaction there is about one molecular equivalent of acid present. This reaction is also illustrated by the reaction diagram:

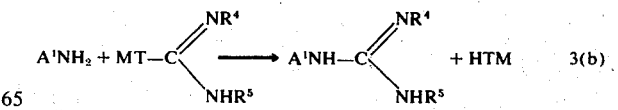

wherein one of $A^1$, $R^4$ and $R^5$ is the Aralkyl group other than unsubstituted benzyl and the other two groups are each methyl, M is as defined above, and the reaction conditions recited above for diagram 3(a) apply.

This type of reaction is also illustrated by the reaction diagram:

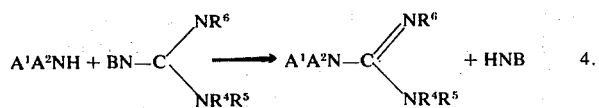  4.

wherein one of $A^1$ and $A^2$ or of $R^4$ and $R^5$ is unsubstituted benzyl and the other and $R^6$ is hydrogen and the two remaining groups are methyl; or $A^1$ and $A^2$ are hydrogen, $R^6$ is unsubstituted benzyl and $R^4$ and $R^5$ are methyl; and BN is an optionally substituted unsaturated heterocyclic group containing at least two nitrogen atoms in the ring, one of which is attached to the carbon atom of the formamidine structure. Examples of BN are pyrazolyl, dialkylpyrazolyl, alkylarylpyrazolyl, dialkylmonohalopyrazolyl, imidazolyl, tirazolyl or tetrazolyl; 3,5-dimethylpyrazol - 1 - yl is preferred.

The same type of reaction is also illustrated by:-

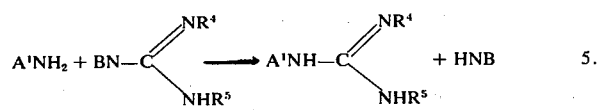  5.

wherein one of $A^1$, $R^4$ and $R^5$ is the Aralkyl group other than unsubstituted benzyl and the remaining two groups are each methyl, and BN is an optionally substituted unsaturated heterocyclic group containing at least two nitrogen atoms in the ring, as exemplified above, one of which is attached to the carbon atom of the formamidine structure.

A further example for producing the compound of formula (I) containing the N', N'-dimethyl group, is the reaction of dimethylamine with N-benzylcyanamide, which may be represented by the reaction diagram:

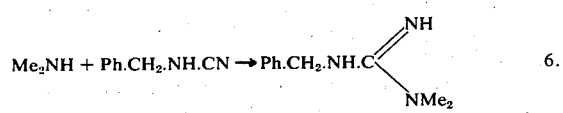  6.

As another example, the compounds of formula (I) wherein there is present a N,N'-dimethyl group, may be produced by the reaction of an appropriate amine or a salt thereof with an isocyandihalide, an imidocarbonate or imidothiocarbonate, or a diimide. These reactions may be illustrated by the following reaction diagram:

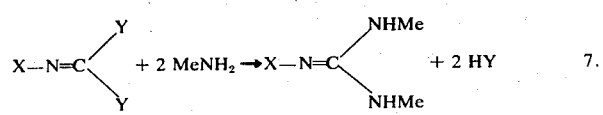  7.

where X is an Aralkyl group other than unsubstituted benzyl, and Y is a halogen atom or the group MT- where T and M are as defined above; preferably M is an alkyl group of one to four carbon atoms. When Y is a halogen atom it is preferably a chlorine or bromine atom; this reaction is conveniently carried out in an alcohol, especially preferred being an alcohol such as methanol or ethanol containing an inert solvent such as ether or benzene, and the methylamine is desirably used in excess. When Y is the group, MT— then T is preferably oxygen and M preferably an alkyl group of one to six carbon atoms, especially ethyl or methyl; this reaction is normally carried out in an aqueous alcoholic medium, whilst the preferred temperature range is from 10° to 30°C; and the methylamine is advantageously present as a mixture of the base and an acid addition salt thereof, the molecular proportion of the base exceeding that of the salt. This type of reaction is further illustrated by the reaction diagram:

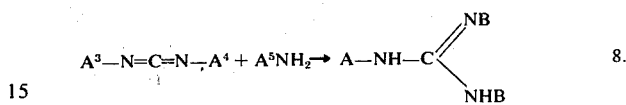  8.

Wherein one of $A^3$, $A^4$ and $A^5$ is the Aralkyl group other than unsubstituted benzyl and the remaining two groups are methyl. These reactions are preferably carried out in the presence of a lower alkanol solvent having 1 to 4 carbon atoms.

Pharmaceutically acceptable acid addition salts of the compounds of formula (I) may also be obtained from the corresponding base or other salts. For example, the sulphate may be prepared from the iodide or chloride by reaction with silver sulphate, or from the base by reaction with sulphuric acid. In an analogous manner salts may be converted to the corresponding base by treatment with a convenient base, such as sodium hydroxide.

The present invention also provides the above methods of preparation of non-toxic acid addition salts of the compounds of formula (I).

The compounds of formula (I) may be presented in any pharmaceutical composition in association with a pharmaceutically acceptable carrier therefor. One or more carriers may be included in a composition of this invention, each carrier performing one or more functions as an excipient in the composition, for example acting as a diluting agent, a suspending agent, a solvent, or a variety of other well established functions. Compositions for oral or parenteral administration are preferred, and oral administration is especially preferred.

For oral administration, fine powders or granules of the compounds of formula (I) may contain diluting, dispersing and/or surface active agents, and may be presented in a draught in water or in a syrup, in capsules or cachets in the dry state or in a non-aqueous suspension, when suspending agents may be included; in tablets, when binders and lubricants may be included; or in a suspension in water, a syrup, an oil or a water/oil emulsion. Where desirable or necessary, flavouring, preserving, suspending, thickening or emulsifying agents can be included. Tablets and granules are preferred, and these may be coated.

For parenteral administration, the compounds of formula (I) may be presented in a sterile form, for example in aqueous injection solutions which may contain antioxidants, buffers, bacteriostats, agents which solubilise a relatively insoluble compound, and solutes which render the salt isotonic with the blood; in aqueous suspensions when suspending and thickening agent may also be included; or in non-aqueous solutions and suspensions if the particular compound selected is affected by water.

The compositions of the invention may be made by any of the well established techniques of pharmaceutical formulation. For example, powders may be made by the intimate admixture of a compound of formula (I) with a solid, finely divided carrier; tablets may be made by compressing such a powder or by compressing granules of a compound of formula (I); and injectable solutions may be made by solubilising a compound of formula (I) in pyrogen-free water, sealing the solution is a container to produce a sterile composition.

Dosages of the compounds of formula (I) are preferably in the range 1 to 10 mg/kg of the bases, especially about 4 mg/kg. Desirably the pharmaceutical compositions are presented in unit dosage form, usually containing in the range 100 to 600 mg. of base.

The following examples illustrate the invention.

EXAMPLE 1

N-p-Iodobenzyl-N', N''-dimethylguanidine sulphate

A solution of p-iodobenzylamine hydrochloride (13.5 g) in water (400 ml.) was mixed with diethylaminocarbonate (5.85 g) dissolved in water (25 ml.). The oil which separated was extracted with ether and the product obtained by evaporation in vacuo.

The crude diethyl N-p-iodobenzyliminocarbonate so obtained (12.5 g) was stirred for 1 hour at room temperature with 33% ethanolic methylamine (100 ml.) and methylamine sulphate (3.01 g) dissolved in water (40 ml.). After standing overnight, the solution was evaporated in vacuo and the residue crystallised from methanol-ether to yield the N-p-iodobenzyl-N',N''-dimethylguanidine sulphate.

EXAMPLE 2

Tablets (0.555 g) of N-p-iodobenzyl-N',N''-dimethylguanidine sulphate were made by mixing the salt (0.25 g) in a fine powder with lactose (0.25 g) and starch (0.05 g), granulating the mixture with alcohol or alcoholic polyvinyl pyrrolidone or a mixture of equal parts of alcohol and water, drying the granules at 40°, adding magnesium stearate (0.010 g.) as a lubricant and compressing the mixture.

EXAMPLE 3

Injection solutions containing N-p-iodobenzyl-N',-N''-dimethylguanidine sulphate in Water for Injection (0.2 g. per ml.) were made by autoclaving the solution at 15 lb. steam pressure for 30 minutes in unit dose ampoules or multidose containers. For the latter, the Water for Injection contained benzyl alcohol (1.0%), phenol (0.5%) or chlorocresol (0.1%).

EXAMPLE 4

N-Benzyl-N',N',S-trimethylisothiourea hydriodide (3.36 g.) was warmed with a solution of 0.880 ammonia (20 ml.) and ethanol (10 ml.) for 4¼ hours and then evaporated to about 5 ml. in vacuo. The residual oil was dissolved in dilute hydrochloric acid and washed with ether. The clear acid solution was basified with excess concentrated sodium hydroxide solution and extracted with ether. The ether extracts were evaporated to dryness, the residue dissolved in n-propanol, and an excess of oxalic acid was added, followed by ether and ethyl acetate. The crystalline product was recrystallised from n-propanol/ethyl acetate to give N-benzyl-N',N'-dimethylguanidine hydrogen oxalate, m.p. 131°–133°.

EXAMPLE 5

Tablets (0.555 g.) of N-benzyl-N',N'-dimethylguanidine hydrogen oxalate were made by mixing the salt (0.25 g.) in a fine powder with lactose (0.25 g.) and starch (0.05 g.), granulating the mixture with alcohol or alcoholic polyvinyl pyrrolidone or a mixture of equal parts of alcohol and water, drying the granules at 40°, adding magnesium stearate (0.010 g.) as a lubricant end compressing the mixture.

EXAMPLE 6

Injection solutions containing N-benzyl-N',N'-dimethylguanidine hydrogen oxalate in Water for Injection (0.2 g. per ml.) were made by autoclaving the solution at 15 lb. steam pressure for 30 minutes in unit dose ampoules or multi-dose containers. For the latter, the Water for Injection contained benzyl alcohol (1.0%), phenol (0.5%) or chlorocresol (0.1%).

EXAMPLE 7

Injection solutions containing N-$\beta$-phenethyl-N',N''-dimethylguanidine sulphate in Water for Injection (0.2 g. per ml.) were made by autoclaving the solution at 15 lb. steam pressure for 30 minutes in unit dose ampoules or multidose containers. For the latter, the Water for Injection contained benzyl alcohol (1.0%), phenol (0.5%) or chlorocresol (0.1%).

EXAMPLE 8

Tablets (0.555 g.) of N-$\beta$-phenethyl-N',N''-dimethylguanidines sulphate were made by mixing the salt (0.25 g.) in a fine powder with lactose (0.25 g.) and starch (0.05 g.), granulating the mixture with alcohol or alcoholic polyvinyl pyrrolidone or a mixture of equal parts of alcohol and water, drying the granules at 40°, adding magnesium stearate (0.010 g.) as a lubricant and compressing the mixture.

EXAMPLE 9

To p-hydroxybenzylamine (15 g.) was added a solution of methyl isothiocyanate (7.76 g.) in ether (15 ml.) and the reaction mixture warmed on the steam bath for 5–10 minutes; the resulting mixture was cooled and further diluted with ether. The separating crystalline N-p-hydroxy-benzyl-N'-methylthiourea was collected and after crystallisation from water it melted at 156°–159°C.

N-p-Hydroxybenzyl-N'-methylthiourea (7.3 g.) was dissolved in acetone (110 ml.), methyl iodide (3.65 ml.) was added, and the solution boiled under reflux for one hour. Addition of ether then precipitated crystalline N-p-hydroxybenzyl-N',S-dimethylisothiourea hydriodide; after recrystallisation from isopropanol/ether mixture it had melting point 126°–129°C.

This hydriodide (9.74 g.) was mixed with 33% ethanolic methylamine (50 ml.) and boiled under reflux for six hours. The solution was evaporated to dryness and the solid residue recrystallised twice from isopropanol/ether mixture to yield N-p-hydroxybenzyl-N',N''-dimethylguanidine hydriodide, melting point 151°–157°C. This (6.99 g.) was dissolved in water (50 ml.) and added slowly to a solution of silver sulphate (3.22 g.) in hot water (400 ml.); after cooling and filtering off the precipitated silver iodide, the solution was evaporated to dryness. The resulting crude solid, N-p-hydroxybenzyl-N',N''-dimethylguanidine sulphate, was purified by extracting with hot ethanol, the residue having a melting point of 248°–250°C.

EXAMPLE 10

2-phenylethylamine (2.4 g.), N,N',S-trimethylisothiourea hydriodide (4.92 g.) and ethanol (70 ml.), were boiled together under reflux for eight hours; methyl mercaptan was evolved. The resulting solution was evaporated to dryness and the residue recrystallised from methanol/ether mixture to yield N,N'-dimethyl-N''-2-phenylethylguanidine hydriodide, melting point 156°–160°C.

This hydriodide was dissolved in water, strongly basified with 10N-sodium hydroxide solution, and the oily base extracted three times with benzene. The combined extracts were dried over solid potassium hydroxide, filtered and evaporated. The residual base was dissolved in a little ethanol and an equal weight of oxalic acid in ethanol was added. Evaporation of the solution and agitation of the residue with ethyl acetate afforded the crystalline N,N'-dimethyl-N''-2-phenylethylguanidine hydrogen oxalate which melted at 125°–127° after recrystallisation from isopropanol-/ethyl acetate mixture.

EXAMPLE 11

Tablets and injection solutions of N-p-hydroxybenzyl-N',N''-dimethylguanidine sulphate were prepared in the manner described in Examples 2 and 3.

EXAMPLE 12

N-p-iodobenzyl-N',N''-dimethylguanidine sulphate was dissolved in water, strongly basified with sodium hydroxide, and the base extracted with ether. The ether, on evaporation, gave an oil which was dissolved in water, neutralised with dilute hydriodic acid and evaporated, to yield N-p-iodobenzyl-N',N''-dimethylguanidine hydriodide, m.p. 235°–239°, after recrystallisation from methanol-ether.

What is claimed is:

1. A method for the treatment of cardiac arrhythmias in a mammal which has had cardiac arrythmias which comprises the administration to the mammal of a non-toxic, effective antiarrhythmic treatment amount of a pharmaceutically acceptable acid addition salt of the compound of the formula

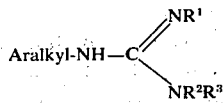

wherein 'Aralkyl' is selected from the group consisting of unsubstituted benzyl and β-phenethyl, two of the groups R¹, R² and R³ are methyl and the third group is hydrogen, provided always that R² and R³ are both methyl and R¹ is hydrogen when 'Aralkyl' is unsubstituted benzyl.

2. A method according to claim 1 wherein the amount is 1 to 10 mg. of the compound per kg. mammal bodyweight calculated as the base.

3. A method as claimed in claim 1 in which the amount is 100 to 600 mg. calculated as base.

4. A method according to claim 1 in which the compound is in the form of an acid addition salt selected from the group consisting of the chloride, sulphate and p-toluenesulphonate salts.

5. A method of treatment of cardiac arrhythmias in a mammal which has had cardiac arrythmias which comprises administering to the mammal an effective cardiac arrhythmia treatment amount of a pharmaceutically acceptable acid addition salt of N-benzyl-N',N'-dimethylguanidine.

6. A method according to claim 5 wherein the effective amount is 1 to 10 mg. of the base /kg. of mammal bodyweight.

7. A method according to claim 6 wherein the mammal is a human.

8. A method according to claim 5 wherein the mammal is a human.

9. A method according to claim 5 wherein the arrhythmia is ventricular fibrillation.

10. A method according to claim 6 wherein the arrhythmias which are treated are ventricular fibrillations or atrial fibrillations.

11. A method according to claim 10 wherein the mammal is a human.

12. A method according to claim 5 wherein the arrhythmias which are treated are ventricular or atrial fibrillations.

13. A method according to claim 12 wherein the mammal is a human.

14. A method according to claim 9 in which an effective amount is 1 to 10 mg. of the base /kg. of mammal bodyweight.

15. A method according to claim 14 in which the mammal is a human.

16. A method according to claim 1 in which the compound is N-β-phenethyl-N',N''-dimethylguanidine.

17. A method according to claim 16 in which the amount is 1 to 10 mg. of the compound per /kg. mammal bodyweight calculated as base.

18. A method according to claim 16 in which the amount is 100 to 600 mg. calculated as base.

19. The method of claim 16 in which the arrythmias are ventricular or atrial fibrillations.

20. The method of claim 19 in which the arrythmias are ventricular fibrillations.

21. The method of claim 20 in which the amount is 100 to 600 mg. calculated as base.

22. A pharmaceutical composition in solid dosage unit form adapted for administration to treat or suppress arrhythmias, comprising per dosage unit an effective arrhythmia treatment or suppression amount of a pharmaceutically acceptable salt of N-benzyl-N',N'-dimethylguanidine and a therapeutically acceptable carrier therefor.

23. A pharmaceutical composition according to claim 22 in a form adapted for oral administration.

24. A pharmaceutical composition according to claim 23 in the form of a tablet.

25. A pharmaceutical composition according to claim 22 in the form of a discrete dosage unit containing 100 to 600 mg. of the base.

26. A pharmaceutical composition according to claim 22 wherein the acid addition salt is selected from the group consisting of the chloride, sulphate and p-toluenesulphonate salts.

* * * * *